US010991982B2

United States Patent
Wagner et al.

(10) Patent No.: US 10,991,982 B2
(45) Date of Patent: Apr. 27, 2021

(54) ELECTROLYTE-ADDITIVE FOR LITHIUM-ION BATTERY SYSTEMS

(71) Applicant: WESTFÄLISCHE WILHELMS-UNIVERSITÄT MÜNSTER, Münster (DE)

(72) Inventors: Ralf Wagner, Münster (DE); Stephan Röser, Münster (DE); Sebastian Brox, Dülmen (DE); Andreas Lerchen, Münster (DE); Frank Glorius, Münster (DE); Martin Winter, Münster (DE)

(73) Assignee: WESTFÄLISCHE WILHELMS-UNIVERSITÄT MÜNSTER, Münster (DE)

( * ) Notice: Subject to any disclaimer, the term of this patent is extended or adjusted under 35 U.S.C. 154(b) by 15 days.

(21) Appl. No.: 16/486,423

(22) PCT Filed: Feb. 13, 2018

(86) PCT No.: PCT/EP2018/053555
§ 371 (c)(1),
(2) Date: Aug. 15, 2019

(87) PCT Pub. No.: WO2018/149823
PCT Pub. Date: Aug. 23, 2018

(65) Prior Publication Data
US 2020/0112058 A1    Apr. 9, 2020

(30) Foreign Application Priority Data
Feb. 17, 2017 (DE) .......................... 102017103334.3
Apr. 4, 2017 (DE) .......................... 102017107257.8

(51) Int. Cl.
| H01M 10/0567 | (2010.01) |
| H01M 10/0568 | (2010.01) |
| H01M 10/0569 | (2010.01) |
| H01M 10/0525 | (2010.01) |
| C07D 273/01 | (2006.01) |

(52) U.S. Cl.
CPC ...... *H01M 10/0567* (2013.01); *C07D 273/01* (2013.01); *H01M 10/0525* (2013.01); *H01M 10/0568* (2013.01); *H01M 10/0569* (2013.01); *H01M 2300/0025* (2013.01)

(58) Field of Classification Search
CPC ......... H01M 10/0525; H01M 10/0567; H01M 10/0568; H01M 10/0569; H01M 2300/0025
See application file for complete search history.

(56) References Cited

U.S. PATENT DOCUMENTS 10,784,530 B2 * 9/2020 Dahn ................ H01M 10/0567
2014/0017547 A1    1/2014 Eichinger

FOREIGN PATENT DOCUMENTS

DE    10 2010 020 992 A1    11/2011

OTHER PUBLICATIONS

S. Röser, A. Lerchen, L. Ibing, X. Cao, J. Kasnatscheew, F. Glorius, M. Winter, R. Wagner. Highly Effective Solid Electrolyte Interphase-Forming Electrolyte Additive Enabling High Voltage Lithium-Ion Batteries, Chem. Mater. 2017, 29, 7733-7739.*
Translation of International Search Report from corresponding International Application No. PCT/EP2018/053555 dated Aug. 20, 2019.
Min Sik Park et al. "Design of novel additives and nonaqueous solvents for lithium-ion betteries through screening of cyclic organic molecules: an ab initio study of redox potentials" Physical Chemistry Chemical Physics., Jan. 1, 2014; vol. 16; pp. 22391-22398.
Yujie Liang et al. "Cationic Cobalt (III)-Catalyzed Aryl and Alkenyl C-H Amidation: A Mild Protocol for the Modification of Purine Derivatives" Chemistry—A European Journal Communication. Sep. 29, 2015; vol. 21; pp. 16395-16399.
Juhyeon Park et al. "Comparative Catalytic Activity of Group 9 [Cp*M$^{III}$] Complexes: Cobalt-Catalyzed C-H Amidation of Arenes with Dioxazolones as Amidating Reagents" Angewandte Chemie International Edition; Sep. 25, 2015; vol. 54; pp. 14103-14107.
Zhang et al. "A review of electrotype additives for lithium-ion batteries" Journal of Power Sources; Nov. 2006; vol. 162; pp. 1379-1394.
International Search Report from corresponding International Application No. PCT/EP2018/053555 dated May 2, 2019.
German Search Report from corresponding German Application No. DE 10 2017 103 334.3 dated Oct. 6, 2017.

* cited by examiner

*Primary Examiner* — Carlos Barcena
(74) *Attorney, Agent, or Firm* — Davidson, Davidson & Kappel, LLC (57) ABSTRACT

The invention relates to the use of compounds according to general formula (1), in particular 1,4,2-dioxoazol-5-on-derivatives, as additives in electrolytes for electrochemical energy sources such as lithium-ion-batteries, and compounds containing electrolytes according to general formula (1), in particular 1,4,2-dioxoazol-5-on-derivatives.

17 Claims, 3 Drawing Sheets

ELECTROLYTE-ADDITIVE FOR LITHIUM-ION BATTERY SYSTEMS

This application is a U.S. national phase application under 35 U.S.C. of § 371 of International Application No. PCT/EP2018/053555, filed Feb. 13, 2018, which claims priority of German Patent Application No. DE 10 2017 107 257.8, filed Apr. 4, 2017, and German Patent Application No. DE 10 2017 103 334.3, filed Feb. 17, 2017, the disclosures of which are hereby incorporated by reference herein.

The invention relates to the field of lithium ion batteries.

Lithium ion batteries (secondary batteries) are at present the leading technology in the field of rechargeable batteries, especially in the field of portable electronics. Conventional lithium ion batteries use an anode composed of carbon, usually graphite. Charge transport occurs via an electrolyte which comprises a lithium salt which is dissolved in a solvent. Various electrolytes and electrolyte salts are known in the prior art. Conventional lithium ion batteries at present usually employ lithium hexafluorophosphate ($LiPF_6$).

Suitable electrolytes are characterized in that the formation of a solid-electrolyte phase boundary, known as the solid electrolyte interphase (SEI), on an electrode is induced. In the case of graphite anodes, reductive decomposition of the electrolyte occurs and the reaction products can form an adhering film which is electronically insulating but conducts lithium ions on the anode. The solid electrolyte interphase then prevents the electrode material from reacting further with the electrolyte and in this way protects the electrolyte from further reductive decomposition and the anode from destruction by the solvent. Particularly when graphite anodes are used, the formation of such a film is necessary for reliable operation of the lithium ion battery.

However, the reductive decomposition of the solvent propylene carbonate (IUPAC name 4-methyl-1,3-dioxolan-2-one) does not lead to formation of a solid electrolyte interphase. Thus, the reductively induced evolution of gas within the graphite layers, induced by cointercalation of propylene carbonate, brings about breaking-apart ("exfoliation") and irreversible destruction of the active material. This limits the utility of propylene carbonate, despite better thermal and physicochemical properties compared to ethylene carbonate, for lithium ion technology. Furthermore, propylene carbonate can serve as model system for electrolytes which likewise display reductive decomposition without SEI formation and exfoliation of graphite.

Further electrolytes containing dioxolanes as organic solvents are known in the prior art. The document DE 10 2010 020 992 A1 discloses, for example, solvents comprising ethylene carbonate, propylene carbonate, butylene carbonate and further compounds such as 3-methyl-1,3-oxazolidin-2-one, and also mixtures of two or more of these solvents.

Suppressing the exfoliation of graphite and the reductive decomposition of the solvent by use of highly concentrated electrolytes has already been proposed. However, the use of highly concentrated electrolytes, also known as "solvent-in-salt" electrolytes, is not economical since this approach requires many times the amount of electrolyte salt normally needed.

Furthermore, the viscosity of the electrolyte is increased greatly by the concentration (usually >3 mol $l^{-1}$), which leads to a noticeable decrease in the conductivity and the performance of the battery. Furthermore, it is to be expected that on decreasing the operating temperature, the system will go below the solubility product of the electrolyte salt in the electrolyte solution, leading to precipitation of the salt in the interior of the batteries. In addition, the density and therefore the total mass of the electrolyte increases at a constant volume with an increasing addition of electrolytes salt. This likewise leads to the specific energy density (Ah $kg^{-1}$) of the battery as total system decreasing.

Furthermore, the use of suitable performance additives has been proposed. Here, vinylene carbonate (VC) and fluoroethylene carbonate (FEC) are particularly important in commercial batteries. However, the conventionally used additive vinylene carbonate can be used only up to a final voltage of not more than 4.7 V in lithium ion batteries, since oxidative decomposition otherwise occurs. There is therefore a need for SEI-forming electrolyte additives having increased oxidative stability, especially for the development of high-voltage electrolytes.

It was therefore an object of the present invention to provide an electrolyte which overcomes at least one of the abovementioned disadvantages of the prior art. In particular, it was an object of the present invention to provide a compound which assists the formation of a solid electrolyte interphase.

This object is achieved by an electrolyte for an electrochemical energy store comprising an electrolyte salt and a solvent, wherein the electrolyte comprises at least one compound of the general formula (1) as indicated below:

(1)

where:

X is C, S or S=O;

$R^1$ is selected from the group comprising CN, $C_1$-$C_{10}$-alkyl, $C_1$-$C_{10}$-alkoxy, $C_3$-$C_7$-cycloalkyl, $C_6$-$C_{10}$-aryl and/or —CO—O—$R^2$, where the alkyl, alkoxy, cycloalkyl and aryl groups are each unsubstituted or monosubstituted or polysubstituted by at least one substituent selected from the group comprising F, $C_{1-4}$-alkyl and/or CN; and $R^2$ is selected from the group comprising $C_1$-$C_{10}$-alkyl, $C_3$-$C_7$-cycloalkyl and/or $C_6$-$C_{10}$-aryl.

Further advantageous embodiments of the invention can be derived from the dependent claims and the secondary claims.

It has surprisingly been found that compounds of the general formula (1) form a solid electrolyte interphase (SEI) on a graphite electrode. Use of a compound of the general formula (1) in electrolytes thus allows the use of solvents such as propylene carbonate, which alone do not form a solid electrolyte interphase, in electrochemical energy stores such as lithium ion batteries. It could be established that the compounds of the general formula (1) can contribute to forming a stable solid electrolyte interphase which can protect graphite anodes against exfoliation and also protect the bulk electrolyte against continuous reductive decomposition over at least 50 charging and discharging cycles. It is here particularly advantageous that the decomposition of the compounds of the general formula (1), e.g. 3-methyl-1,4,2-dioxoazol-5-one, occurs at higher potentials than that of vinylene carbonate. The higher oxidative stability of the SEI-forming compounds of the general formula (1) thus makes use in high-voltage batteries possible.

An electrolyte according to the invention can thus advantageously be used as high-voltage electrolyte. Without wishing to be tied to a particular theory, it is assumed that a polymerization reaction involving the double bond of the 1,4,2-dioxoazol-5-one derivatives of the general formula (1) participates in the presumed reaction mechanism of the formation of the SEI and thus is important for the advantageous properties of the compounds.

The term "$C_1$-$C_{10}$-alkyl" encompasses, unless indicated otherwise, straight-chain or branched alkyl groups having from 1 to 10 carbon atoms. The term "$C_6$-$C_{10}$-aryl" refers to aromatic radicals having from 6 to 10 carbon atoms. The term "aryl" preferably encompasses carbocycles. $C_6$-$C_{10}$-Aryl groups are preferably selected from the group comprising phenyl and/or naphthyl, preferably phenyl. $C_3$-$C_7$-Cycloalkyl groups are preferably selected from the group comprising cyclopentyl und/or cyclohexyl. $C_1$-$C_5$-Alkoxy groups are preferably selected from the group comprising methoxy, ethoxy, linear or branched propoxy, butoxy and/or pentoxy.

The substituent X can be carbon or sulfur or an S=O group. X is preferably carbon.

The substituent $R^1$ is preferably selected from the group comprising CN, $C_1$-$C_5$-alkyl, $C_1$-$C_5$-alkoxy, $C_5$-$C_6$-cycloalkyl and/or phenyl, where the alkyl, alkoxy, cycloalkyl and phenyl groups are each unsubstituted or monosubstituted or polysubstituted by fluorine. Fluorinated substituents $R^1$ can assist the formation of the solid electrolyte interphase. In particular, the stability of the electrolyte additive can be matched in a targeted manner to the requirements of a lithium ion battery by means of fluorination. In preferred embodiments, $R^1$ is selected from the group comprising CN and/or $C_1$-$C_5$-alkyl or phenyl which are unsubstituted or monosubstituted or polysubstituted by fluorine. Such groups $R^1$ can advantageously assist the reactions of the double bond which lead to formation of a solid electrolyte interphase (SEI) on an electrode. $C_1$-$C_5$-Alkyl groups are, in particular, selected from the group comprising methyl, ethyl, propyl, isopropyl, butyl, isobutyl, tert-butyl, pentyl, isopentyl, tert-pentyl and/or neopentyl. In further preferred embodiments, $R^1$ is selected from the group comprising CN, tert-butyl, phenyl and/or $C_1$-$C_2$-alkyl which is unsubstituted or monosubstituted or polysubstituted by fluorine. In particularly preferred embodiments, $R^1$ is selected from the group comprising $CH_3$, $CF_3$, CN, tert-butyl and/or phenyl.

If $R^1$ is a —CO—O—$R^2$ group, $R^2$ is preferably selected from the group comprising $C_1$-$C_5$-alkyl, $C_5$-$C_6$-cycloalkyl and/or phenyl.

The electrolyte preferably comprises at least one compound of the general formula (1) in which:
X is C, S or S=O; and/or
$R^1$ is selected from the group comprising CN, $C_1$-$C_5$-alkyl, $C_1$-$C_5$-alkoxy, $C_5$-$C_6$-cycloalkyl, phenyl and/or —CO—O—$R^2$, where the alkyl, alkoxy, cycloalkyl and phenyl groups are in each case unsubstituted or monosubstituted or polysubstituted by fluorine, and/or
$R^2$ is selected from the group comprising $C_1$-$C_5$-alkyl, $C_5$-$C_6$-cycloalkyl and/or phenyl.

The electrolyte particularly preferably comprises at least one compound of the general formula (1) in which X is carbon and/or $R^1$ is selected from the group comprising CN, phenyl and/or $C_1$-$C_5$-alkyl, in particular $C_1$-$C_2$-alkyl, which is unsubstituted or monosubstituted or polysubstituted by F. Small alkyl groups advantageously lead to compounds which can contribute to the efficient formation of a solid electrolyte interphase. In preferred embodiments, X is carbon and $R^1$ is selected from the group comprising $CH_3$, $CF_3$, CN, tert-butyl and/or phenyl.

Particular preference is given to X being carbon and the electrolyte comprising at least one 1,4,2-dioxoazol-5-one derivative of the general formula (2)

where:
$R^1$ is selected from the group comprising CN, $C_1$-$C_5$-alkyl, $C_1$-$C_5$-alkoxy, $C_5$-$C_6$-cycloalkyl, phenyl and/or —CO—O—$R^2$, where the alkyl, alkoxy, cycloalkyl and phenyl groups are in each case unsubstituted or monosubstituted or polysubstituted by fluorine, and/or
$R^2$ is selected from the group comprising $C_1$-$C_5$-alkyl, $C_5$-$C_6$-cycloalkyl, and/or phenyl.

Preference is given to 1,4,2-dioxoazol-5-one derivatives in which $R^1$ is selected from the group comprising CN and/or $C_1$-$C_5$-alkyl or phenyl which are unsubstituted or monosubstituted or polysubstituted by fluorine, in particular selected from the group comprising CN, tert-butyl, phenyl and/or $C_1$-$C_2$-alkyl which is unsubstituted or monosubstituted or polysubstituted by fluorine. 1,4,2-Dioxoazol-5-one derivatives, in particular, can advantageously form, in electrolytes, a stable solid electrolyte interphase which can protect graphite anodes against exfoliation and protect the bulk electrolyte against continuous reduction over a cycling time of at least 50 charging and discharging cycles. A particularly preferred 1,4,2-dioxoazol-5-one derivative is 3-methyl-1,4,2-dioxoazol-5-one.

It has been able to be shown that an electrolyte containing 3-methyl-1,4,2-dioxoazol-5-one has a wide oxidative stability window and due to this high stability can thus also be used for applications in which high-voltage electrode materials are present. This represents a particular advantage since conventional SEI formers do not allow graphite anodes to be operated with high-voltage cathode materials in lithium ion batteries having switch-off potentials above 4.5 V vs. Li/Li$^+$. The compounds according to the invention can be used as additive in electrolytes in combination with conventional electrode materials such as $Li(Ni_{1/3}Mn_{1/3}Co_{1/3})O_2$ (NMC (111)) cathodes, $LiFePO_4$ (LFP), $LiMPO_4$ (M=Mn, Ni, Co), $LiMn_2O_4$ (LMO), $LiNi_xMn_yO_4$ (LNMO), $Li(Ni_xCo_yMn_z)O_2$ (x+y+z=1) (NMC(XYZ)), $(Li_2MnO_3)_x(LiMO_2)_{1-x}$ and $Li(Ni_xCo_yAl_z)O_2$ (x+y+z=1) (NCA).

The compounds of the general formula (1) are commercially available or can be prepared by methods with which a person skilled in the art will be familiar.

In preferred embodiments, the electrolyte contains the compound of the general formula (1) in an amount in the range from ≥0.1% by weight to ≤10% by weight, preferably in the range from ≥0.5% by weight to ≤7% by weight, more preferably in the range from ≥3% by weight to ≤5% by weight, based on the total weight of the electrolyte. Figures in % by weight are in each case based on a total weight of the electrolyte of 100% by weight. Figures in percent correspond, if not indicated otherwise, to figures in % by weight.

An electrolyte comprising such proportions of a compound of the general formula (1), in particular 1,4,2-dioxoazol-5-one derivatives such as 3-methyl-1,4,2-dioxoazol-5-one, can advantageously display very good formation of a solid electrolyte interphase. Proportions in the range from ≥3% by weight to ≤5% by weight, based on the total weight of the electrolyte, can advantageously be sufficient for effective passivation of graphite. Such low proportions by weight of an additive allow economical commercial use.

Furthermore, it was able to be established that even electrolytes containing 2% by weight of 3-methyl-1,4,2-dioxoazol-5-one, based on the total weight of the electrolyte, display very good cycling stability at low temperatures. Advantageously, the compounds of the formula (1) such as 3-methyl-1,4,2-dioxoazol-5-one are well suited to low-temperature applications and lithium ion batteries having 3-methyl-1,4,2-dioxoazol-5-one as additive can, in particular, be operated with good cycling stability at low temperatures.

The electrolyte comprises a solvent in addition to at least one electrolyte salt, preferably a lithium salt, and at least one compound of the general formula (1). The solvent preferably serves as solvent for the electrolyte salt or lithium salt.

In preferred embodiments, the electrolyte comprises a solvent selected from the group comprising an unfluorinated or partially fluorinated organic solvent, an ionic liquid, a polymer matrix and/or mixtures thereof.

The electrolyte preferably comprises an organic solvent, in particular a cyclic or linear carbonate. In preferred embodiments, the organic solvent is selected from the group comprising ethylene carbonate, ethyl methyl carbonate, propylene carbonate, dimethyl carbonate, diethyl carbonate, acetonitrile, propionitrile, 3-methoxypropionitrile, glutaronitrile, adiponitrile, pimelonitrile, gamma-butyrolactone, gamma-valerolactone, dimethoxyethane, 1,3-dioxolane, methyl acetate, ethyl acetate, ethyl methanesulfonate, dimethyl methylphosphonate, linear or cyclic sulfone such as ethyl methyl sulfone or sulfolane, symmetrical or unsymmetrical alkyl phosphates and/or mixtures thereof. Further preferred organic solvents are symmetrical or unsymmetrical organosilanes and/or siloxanes. Preference is likewise given to mixtures of symmetrical or unsymmetrical organosilanes and/or siloxanes with one or more solvents selected from the group comprising ethylene carbonate, ethyl methyl carbonate, propylene carbonate, dimethyl carbonate, diethyl carbonate, acetonitrile, propionitrile, 3-methoxypropionitrile, glutaronitrile, adiponitrile, pimelonitrile, gamma-butyrolactone, gamma-valerolactone, dimethoxyethane, 1,3-dioxolane, methyl acetate, ethyl acetate, ethyl methanesulfonate, dimethyl methylphosphonate, linear or cyclic sulfone such as ethyl methyl sulfone or sulfolane and/or symmetrical or unsymmetrical alkyl phosphates.

The electrolyte can, in particular, comprise solvents such as propylene carbonate which without an additive do not lead to formation of a solid electrolyte interphase. For these solvents to be used, addition of the compounds according to the invention is particularly advantageous for forming an effective solid electrolyte interphase. Advantageously, an electrolyte comprising propylene carbonate as solvent can have a comparable oxidative stability and similarly efficient SEI-formation as known electrolytes which can form a solid electrolyte interphase without addition of further compounds when a compound of the general formula (1) is used. The electrolyte preferably comprises propylene carbonate or a mixture comprising propylene carbonate and at least one further organic solvent selected from the group comprising ethylene carbonate, ethyl methyl carbonate, dimethyl carbonate, diethyl carbonate, gamma-butyrolactone, gamma-valerolactone, dimethoxyethane, 1,3-dioxolane, methyl acetate, ethyl acetate, ethyl methanesulfonate, dimethyl methylphosphonate, linear or cyclic sulfone such as ethyl methyl sulfone or sulfolane and/or symmetrical or unsymmetrical alkyl phosphates. The electrolyte more preferably comprises a mixture comprising propylene carbonate and at least one further organic solvent selected from among symmetrical or unsymmetrical organosilanes and siloxanes.

The electrolyte can also be a polymer electrolyte, for example selected from the group comprising polyethylene oxide, polyacrylonitrile, polyvinyl chloride, polyvinylidene fluoride, poly(vinylidene fluoride-co-hexafluoropropylene) and/or polymethyl methacrylate, or a gel polymer electrolyte comprising a polymer and an organic solvent as mentioned above. The electrolyte can likewise be an ionic liquid.

The electrolyte according to the invention comprises at least one electrolyte salt, in particular a lithium salt, in addition to a solvent and at least one compound of the general formula (1).

In preferred embodiments, the electrolyte salt is selected from the group comprising $LiPF_6$, $LiBF_4$, $LiAsF_6$, $LiSbF_6$, $LiCO_4$, $LiPtCl_6$, $LiN(SO_2F)_2$, $LiN(SO_2CF_3)_2$, $LiN(SO_2C_2F_5)_2$, $LiC(SO_2CF_3)_3$, $LiB(C_2O_4)_2$, $LiBF_2(C_2O_4)$ and/or $LiSO_3CF_3$. The lithium salt is preferably $LiPF_6$. The concentration of the lithium salt in the electrolyte can be in customary ranges, for example in the range from $\geq 1.0$ M to $\leq 1.2$ M.

In a preferred embodiment, the electrolyte comprises a compound of the general formula (1), in particular a 1,4,2-dioxoazol-5-one derivative such as 3-methyl-1,4,2-dioxoazol-5-one, at least one lithium salt, preferably $LiPF_6$, and propylene carbonate or a mixture of organic solvents comprising propylene carbonate as solvent. The electrolyte can be produced, for example, by introducing the lithium salt into the solvent and adding the at least one compound of the general formula (1). As an alternative, it is possible firstly to mix the compound of the general formula (1) with the solvent and then to add the lithium salt.

The electrolyte can also contain at least one additive, in particular selected from the group comprising SEI formers and/or flame retardants. For example, the electrolyte can contain a compound of the general formula (1) and also a further SEI former. Suitable additives are, for example, selected from the group comprising fluoroethylene carbonate, chloroethylene carbonate, vinylene carbonate, vinylethylene carbonate, ethylene sulfite, propane sultone, propene sultone, sulfites, preferably dimethyl sulfite and propylene sulfite, ethylene sulfate, propylene sulfate, methylenemethane disulfonate, trimethylene sulfate, butyrolactones optionally substituted by F, Cl or Br, phenylethylene carbonate, vinyl acetate and/or trifluoropropylene carbonate. For example, the electrolyte can contain a compound of the general formula (1) and also a further SEI former selected from the group comprising vinyl carbonate, fluoroethylene carbonate and/or ethylene sulfate. These compounds can improve the battery performance, for example the capacity, the long-term stability or the cycling life.

The electrolyte is particularly suitable for a battery or rechargeable battery, in particular as electrolyte for a lithium ion battery or a rechargeable lithium ion battery.

The present invention further provides an electrochemical energy store, in particular a supercapacitor or electrochemical energy store based on lithium ions, comprising an electrolyte according to the invention as described above. For the purposes of the present invention, the term "energy store" encompasses primary and secondary electrochemical energy storage devices, i.e. batteries (primary stores) and rechargeable batteries (secondary stores). In general language usage, rechargeable batteries are frequently also referred to by the term "battery" used as generic term. Thus, the term lithium ion battery is used synonymously with rechargeable lithium ion battery, unless indicated otherwise. For the purposes of the present invention, the term "electrochemical energy store" also encompasses electrochemical capacitors or supercapacitors (supercaps for short). Electrochemical capacitors, which in the literature are also referred to as double-layer capacitors or supercapacitors, are electrochemical energy stores which compared to batteries display a significantly higher power density and compared to conventional capacitors an energy density which is orders of magnitude higher. Electrochemical energy stores based on lithium ions are preferably selected from the group comprising lithium ion batteries, rechargeable lithium ion batteries and polymer batteries. The energy store is preferably a lithium ion battery or a rechargeable lithium ion battery. Furthermore, the electrochemical energy store is preferably an electrochemical capacitor, in particular supercapacitor. It has been able to be shown that the solid electrolyte interphase formed on a graphite anode was stable over at least 50 cycles. This makes economical operation of rechargeable batteries possible.

The invention further provides a method for forming a solid electrolyte interphase on an electrode of an electrochemical cell comprising an anode, a cathode and an electrolyte, wherein the cell is operated using the electrolyte of the invention, as described above. The solid electrolyte interphase is preferably formed on the anode, in particular a graphite anode, namely the negative electrode. In the discussion of batteries, it has become a convention to use the discharging process as definition for the terms anode and cathode.

The invention further provides for the use of a compound of the general formula (1) as indicated below:

(1)

where:
X is C, S or S=O;
$R^1$ is selected from the group comprising CN, $C_1$-$C_{10}$-alkyl, $C_1$-$C_{10}$-alkoxy, $C_3$-$C_7$-cycloalkyl, $C_6$-$C_{10}$-aryl and/or —CO—O—$R^2$, where the alkyl, alkoxy, cycloalkyl and aryl groups are in each case unsubstituted or monosubstituted or polysubstituted by at least one substituent selected from the group comprising F, $C_{1-4}$-alkyl and/or CN, and
$R^2$ is selected from the group comprising $C_1$-$C_{10}$-alkyl, $C_3$-$C_7$-cycloalkyl, and/or $C_6$-$C_{10}$-aryl,
in an electrochemical energy store, in particular a supercapacitor or an electrochemical energy store based on lithium ions.

The compound of the general formula (1) can advantageously be used as electrolyte additive, in particular as SEI former, in particular in electrolytes which without addition of additive do not form a SEI.

For a description of the compound of the general formula (1), reference is made to the above description. The substituent X is preferably carbon. $R^1$ is preferably selected from the group comprising CN, $C_1$-$C_5$-alkyl, $C_1$-$C_5$-alkoxy, $C_5$-$C_6$-cycloalkyl and/or phenyl, where the alkyl, alkoxy, cycloalkyl and phenyl groups are in each case unsubstituted or monosubstituted or polysubstituted by fluorine. In preferred embodiments, $R^1$ is selected from the group comprising CN and/or $C_1$-$C_5$-alkyl or phenyl which are unsubstituted or monosubstituted or polysubstituted by fluorine. In further preferred embodiments, $R^1$ is selected from the group comprising CN, tert-butyl, phenyl and/or $C_1$-$C_2$-alkyl which is unsubstituted or monosubstituted or polysubstituted by fluorine. In particularly preferred embodiments, $R^1$ is selected from the group comprising $CH_3$, $CF_3$, CN, tert-butyl and/or phenyl. Particular preference is given to X being carbon and/or $R^1$ being selected from the group comprising CN, phenyl and/or $C_1$-$C_5$-alkyl, in particular $C_1$-$C_2$-alkyl, which is unsubstituted or monosubstituted or polysubstituted by F. In preferred embodiments, X is carbon and $R^1$ is selected from the group comprising $CH_3$, $CF_3$, CN, tert-butyl and/or phenyl.

The electrolyte particularly preferably comprises at least one 1,4,2-dioxoazol-5-one derivative of the general formula (2), where $R^1$ is selected from the group comprising CN, $C_1$-$C_5$-alkyl, $C_1$-$C_5$-alkoxy, $C_5$-$C_6$-cycloalkyl, phenyl and/or —CO—O—$R^2$, where the alkyl, alkoxy, cycloalkyl and phenyl groups are in each case unsubstituted or monosubstituted or polysubstituted by fluorine, and/or $R^2$ is selected from the group comprising $C_1$-$C_5$-alkyl, $C_5$-$C_6$-cycloalkyl, and/or phenyl. Particular preference is given to 1,4,2-dioxoazol-5-one derivatives in which $R^1$ is selected from the group comprising CN and/or $C_1$-$C_5$-alkyl or phenyl which are unsubstituted or monosubstituted or polysubstituted by fluorine, in particular selected from the group comprising CN, tert-butyl, phenyl and/or $C_1$-$C_2$-alkyl which is unsubstituted or monosubstituted or polysubstituted by fluorine. 1,4,2-Dioxoazol-5-one derivatives, in particular, can advantageously form, in electrolytes, a stable solid electrolyte interphase which can protect graphite anodes against exfoliation and also the bulk electrolyte against continuous reductive decomposition over a cycling time of at least 50 charging and discharging cycles. A particularly preferred 1,4,2-dioxoazol-5-one derivative is 3-methyl-1,4,2-dioxoazol-5-one.

Examples and figures which serve to illustrate the present invention are described below.

EXAMPLE 1

Preparation of 3-methyl-1,4,2-dioxoazol-5-one

The synthesis was carried out as described by S. Chang et al. in J. Am. Chem. Soc. 2015, 137, pages 4534-4542. For this purpose, 50 mmol of acetohydroxamic acid (Sigma-Aldrich) were dissolved in 500 ml of dichloromethane. 50 mmol of 1,1'-carbonyldiimidazole (Combi-Blocks) were added thereto all at once at room temperature (20° C.±2° C.). After stirring for 16 hours, the reaction mixture was quenched with 300 ml of 1 M HCl, extracted three times with 150 ml in each case of dichloromethane and dried over magnesium sulfate. The solvent was removed under reduced pressure and 3-methyl-1,4,2-dioxoazol-5-one was obtained as a colorless, slightly yellowish oil.

The reaction product obtained was examined by means of $^1$H- and $^{13}$C-NMR, and the $^1$H and $^{13}$C signals corresponded to the expected values for 3-methyl-1,4,2-dioxoazol-5-one.

EXAMPLE 2

Determination of the Specific Capacity in a Graphite/Li Half Cell

The determination of the specific capacity in half cells was carried out using a three-electrode cell (Swagelok® type). Graphite electrodes (SFG6L, Imerys SA) were utilized as electrodes. A polymer nonwoven (Freudenberg SE, FS2226) was used as separator. Lithium foil (Rockwood Lithium, battery unit) served as reference electrode and counterelectrode.

An electrolyte containing 1 M LiPF$_6$ (BASF, battery purity) and 5% by weight of 3-methyl-1,4,2-dioxoazol-5-one obtained from example 1 was produced by dissolving the required amount of LiPF$_6$ in propylene carbonate (PC, BASF, battery purity) and adding the appropriate amount of 3-methyl-1,4,2-dioxoazol-5-one. Comparative electrolytes containing 1 M LiPF$_6$ in propylene carbonate and also a mixture of ethylene carbonate (BASF, battery purity) and dimethyl carbonate (BASF, battery purity) (EC:DMC) in a weight ratio of 1:1 were produced in the same way.

Figure 1:
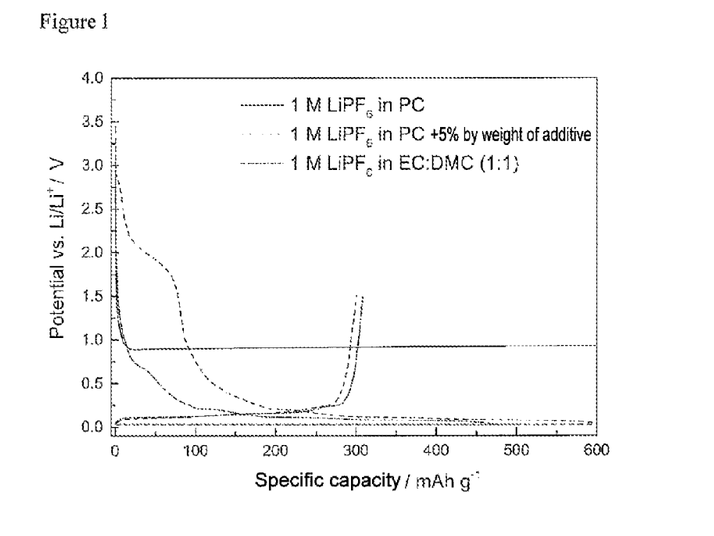
FIG. 1 shows the first cycle of a graphite anode in a graphite/lithium half cell using an electrolyte solution as per one embodiment of the invention containing 1 M $LiPF_6$ and 5% by weight of 3-methyl-1,4,2-dioxoazol-5-one (additive) in propylene carbonate (PC) and also comparative electrolytes containing 1 M $LiPF_6$ in propylene carbonate or a 1:1 mixture of ethylene carbonate and dimethyl carbonate (EC:DMC). The potential is plotted against the specific capacity.

The first charging process and the first discharging process in the range from 0.025 V to 1.5 V vs. Li/Li$^+$ at a C rate of 0.2C was studied. In addition, the potential was kept constant at 0.025 V vs. Li/Li$^+$ for one hour. FIG. 1 shows the first cycle of the graphite/lithium half cell for the electrolytes examined. As can be seen from FIG. 1, the comparative electrolyte 1 M LiPF$_6$ in propylene carbonate did not show any reversible capacity. The addition of 5% by weight of 3-methyl-1,4,2-dioxoazol-5-one to this electrolyte based on propylene carbonate made reversible cycling possible, corresponding to the positive control of the comparative electrolyte containing 1 M LiPF$_6$ in a 1:1 mixture of ethylene carbonate and dimethyl carbonate.

EXAMPLE 3

Determination of the Oxidative Electrochemical Stability in an LMO/Li Half Cell

The determination of the oxidative stability of the electrolytes in half cells was carried out by means of linear sweep voltammetry. In this method, the electrode voltage is continuously changed (linear sweep). A three-electrode cell (Swagelok® type) using lithium-manganese oxide (LMO, Customcells GmbH) as working electrode was utilized for this purpose. Lithium foil (Rockwood Lithium, battery purity) served as reference electrode and counterelectrode. A polymer nonwoven (Freudenberg SE, FS2226) was used as separator. To determine the oxidative stability, the potential between working electrode and reference electrode was increased from the no-load voltage to 6 V. The advance rate of the potential was 0.05 mV s$^{-1}$.

The electrolyte containing 1 M LiPF$_6$ and 5% by weight of 3-methyl-1,4,2-dioxoazol-5-one obtained from example 1 was produced by dissolving the necessary amount of LiPF$_6$ in propylene carbonate and adding the appropriate amount of 3-methyl-1,4,2-dioxoazol-5-one, as described in example 2. Comparative electrolytes were produced in the same way, with one comparative electrolyte containing 1 M LiPF$_6$ in a mixture of ethylene carbonate and dimethyl carbonate (EC:DMC) in a weight ratio of 1:1 and a second comparative electrolyte additionally containing 5% by weight of the additive vinylene carbonate (VC, UBE Industries).

Figure 2:
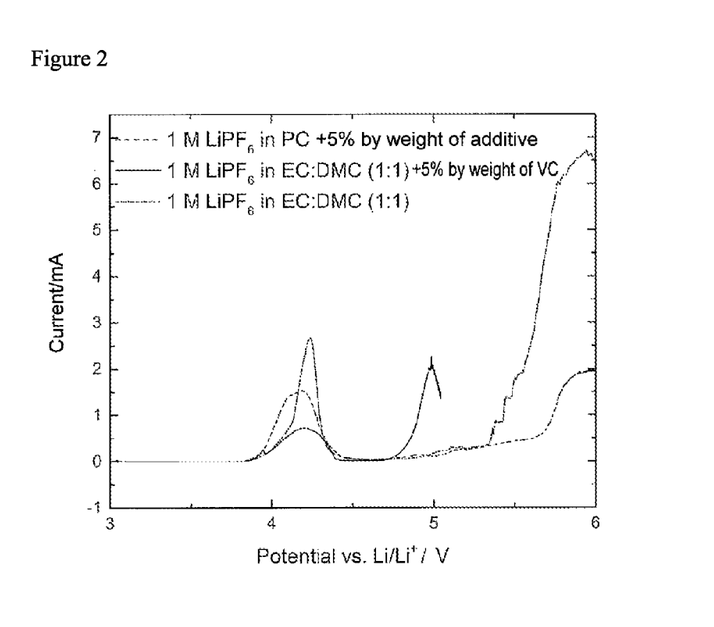
FIG. 2 shows the oxidative stability window in $LiMn_2O_4$/Li half cells of the electrolyte containing 1 M $LiPF_6$ and 5% by weight of 3-methyl-1,4,2-dioxoazol-5-one in propylene carbonate (PC) and also of comparative electrolytes containing 1 M $LiPF_6$ in a 1:1 mixture of ethylene carbonate and dimethyl carbonate (EC:DMC) with or without 5% by weight of VC.

FIG. 2 shows the oxidative stability window of the electrolytes for a potential vs. Li/Li$^+$ in the range from 3 V to 6 V. As can be seen from FIG. 2, the electrolyte containing 5% by weight of 3-methyl-1,4,2-dioxoazol-5-one in propylene carbonate was stable up to 5.6 V vs. Li/Li$^+$, while the electrolytes in ethylene carbonate/dimethyl carbonate with or without addition of 5% by weight of vinylene carbonate were stable up to 4.7 V and 5.3 V vs. Li/Li$^+$, respectively.

The electrolyte according to the invention containing 5% by weight of 3-methyl-1,4,2-dioxoazol-5-one thus shows a significantly higher oxidative stability limit than the electrolyte based on vinylene carbonate. This indicates that 3-methyl-1,4,2-dioxoazol-5-one is oxidized later than vinylene carbonate and thus has a better high-voltage stability. The electrolyte according to the invention containing 5% by weight of 3-methyl-1,4,2-dioxoazol-5-one in propylene carbonate also displays a significantly higher oxidative stability than the reference electrolyte 1 M LiPF$_6$ in a mixture of ethylene carbonate and dimethyl carbonate (EC:DMC). Accordingly, 3-methyl-1,4,2-dioxoazol-5-one is particularly useful for applications in which high-voltage electrode materials are present because of its high oxidative stability.

Effective passivation of graphite can thus be achieved by the use of the dioxazolone derivatives according to the invention in small proportions by weight in the electrolyte. Due to the fact that only 5% by weight of 3-methyl-1,4,2-dioxoazol-5-one in propylene carbonate is sufficient for the formation of a solid electrolyte interphase (SEI) on graphite electrodes, the use of dioxazolones as additive for electrolytes based on propylene carbonate is also economical.

EXAMPLE 4

Examination of the Long-Term Cycling Stability at Constant Current

The examination of the long-term cycling stability was carried out in full cells having a button cell structure (Hohsen Corp., CR2032) using lithium-nickel$_{1/3}$-manganese$_{1/3}$-cobalt$_{1/3}$ oxide (NMC(111), Customcells GmbH) and graphite electrodes (Customcells GmbH). A polymer nonwoven (Freudenberg SE, FS2226) was used as separator. Cycling was carried out in a voltage window of from 4.2 V to 2.8 V. 2 forming cycles were carried out at 0.1C (including holding of the voltage at 4.2 V until the current is <0.05C), followed by 3 conditioning cycles at 0.33C (including holding of the voltage at 4.2 V until the current is <0.05C and a delay step of one hour), followed by 95 1.0C charging/discharging cycles. The measurements at constant current were carried out on a battery tester series 4000 (Maccor) at 20° C.±0.1° C.

The electrolyte containing 1 M LiPF$_6$ and 5% by weight of 3-methyl-1,4,2-dioxoazol-5-one obtained from example 1 was produced by dissolving the necessary amount of LiPF$_6$ in propylene carbonate and adding the appropriate amount of 3-methyl-1,4,2-dioxoazol-5-one, as described in example 2. As comparative electrolyte, a solution of 1 M LiPF$_6$ in a mixture of ethylene carbonate and dimethyl carbonate (EC:DMC) in a weight ratio of 1:1 was produced.

Figure 3:
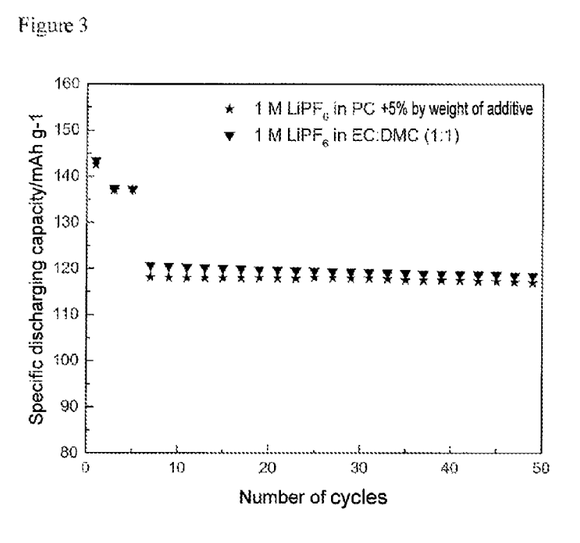
FIG. 3 shows the constant current cycling of an NMC/graphite full cell using the electrolyte solution containing 1 M $LiPF_6$ and 5% by weight of 3-methyl-1,4,2-dioxoazol-5-one (additive) in propylene carbonate (PC) and also a comparative electrolyte containing 1 M $LiPF_6$ in a 1:1 mixture of ethylene carbonate and dimethyl carbonate (EC:DMC) over 50 cycles. The specific discharging capacity in mAh g$^{-1}$ is plotted against the number of cycles. Only every third cycle is shown.
Figure 4:
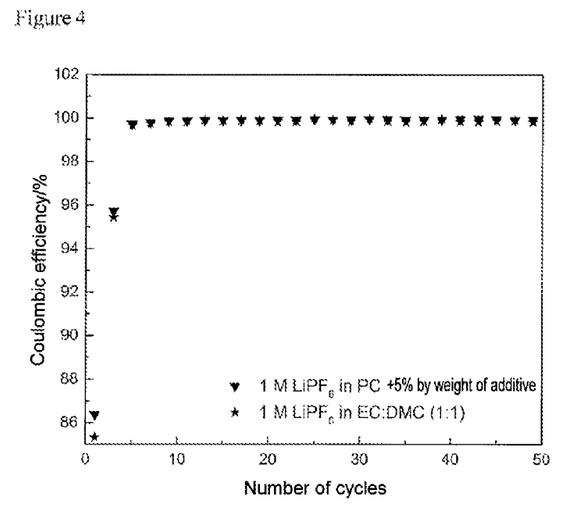
FIG. 4 shows in each case the Coulomb efficiency plotted against the number of cycles for the NMC/graphite full cell using the electrolyte solution containing 1 M $LiPF_6$ and 5% by weight of 3-methyl-1,4,2-dioxoazol-5-one (additive) in propylene carbonate (PC) and also a comparative electrolyte containing 1 M LiPF$_6$ in a 1:1 mixture of ethylene carbonate and dimethyl carbonate (EC:DMC) over 50 cycles. Only every third cycle is shown.

FIG. 3 shows the specific discharging capacity of the NMC/graphite full cell versus the number of cycles and FIG. 4 shows the Coulomb efficiency versus the number of cycles using the respective electrolytes. As FIG. 3 shows, the electrolyte containing 5% by weight of 3-methyl-1,4,2-dioxoazol-5-one displayed only a small decrease in capacity over 50 cycles. The maintenance of capacity in cycle 50 based on the first cycle at 1.0C (cycle 6) was 98.7%. The comparative electrolyte 1 M LiPF$_6$ in a mixture of ethylene carbonate and dimethyl carbonate (EC:DMC) displayed a capacity retention of 98.1%.

Furthermore, it can be seen from FIG. 4 that the Coulombic efficiency in the first cycle was 85.3% for the electrolyte containing 5% by weight of 3-methyl-1,4,2-dioxoazol-5-one. The comparative electrolyte 1 M LiPF$_6$ in a mixture of ethylene carbonate and dimethyl carbonate (EC:DMC) displayed a Coulombic efficiency in the first cycle of 86.3%. The full cell with the electrolyte containing 5% by weight of 3-methyl-1,4,2-dioxoazol-5-one thus displayed good cycling stability, corresponding to the comparative electrolyte 1 M LiPF$_6$ in a mixture of ethylene carbonate and dimethyl carbonate (EC:DMC).

Overall, the results show that 3-methyl-1,4,2-dioxoazol-5-one forms a passivating protective layer which conducts lithium ions on the surface of graphite, is suitable for high-voltage applications and enables lithium ion batteries to be operated with good cycling stability.

EXAMPLE 5

Examination of the Cycling Behavior at Low Temperatures

The examination of the cycling behavior at low temperatures was carried out in full cells having a button cell structure (Hohsen Corp., CR2032) with lithium-nickel-manganese-cobalt oxide (NMC622, Customcells GmbH) and graphite electrodes (Customcells GmbH) using an S240/P20 Separion separator. Cycling was carried out in a voltage window of 2.8-4.2 V. The electrochemical forming at 2×0.1C and the subsequent charging process at 0.1C were carried out at a temperature of 25° C., and the subsequent charging/discharging cycles at 0.3333C were carried out at a temperature of −20° C. The measurements were carried out on a battery tester series 4000 (Maccor).

90 µl of a solution containing 1 M LiPF$_6$ in a mixture of ethylene carbonate, propylene carbonate and diethyl carbonate (EC:PC:DEC) in a weight ratio of 30:5:65 and 2% by weight of 3-methyl-1,4,2-dioxoazol-5-one obtained from example 1 were used as electrolyte. A solution of 1 M LiPF$_6$ in EC:PC:DEC containing 2% by weight of the additive vinylene carbonate (VC, UBE Industries) was used as comparative electrolyte. The electrolytes were produced by dissolving the necessary amount of LiPF$_6$ in the solvent mixture and adding the appropriate amount of additive, as described in example 2.

Figure 5:
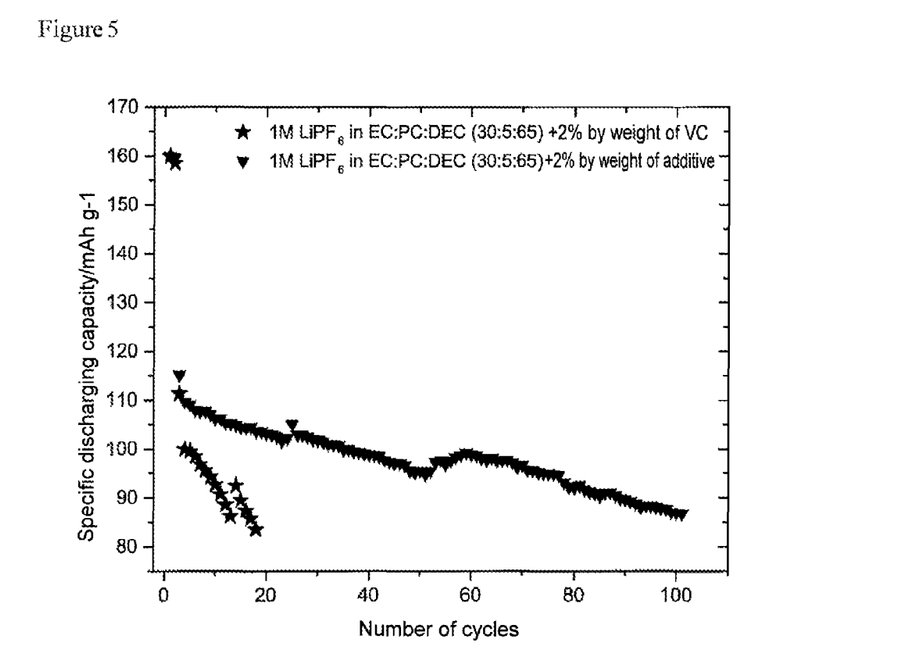
FIG. 5 shows the specific discharging capacity against the number of cycles of a constant current cycling of an NMC622/graphite full cell at −20° C. (after electrochemical forming at 25° C.) using an electrolyte containing 1 M LiPF$_6$ in a 30:5:65% by weight mixture of ethylene carbonate, propylene carbonate and diethyl carbonate (EC:PC:DEC) and 2% by weight of 3-methyl-1,4,2-dioxoazol-5-one (additive) and also a comparative electrolyte containing 2% by weight of vinylene carbonate (VC).

FIG. 5 shows the specific discharging capacity at −20° C., after prior forming at 25° C. for 2 cycles, plotted against the number of cycles for the electrolyte containing 2% by weight of 3-methyl-1,4,2-dioxoazol-5-one (additive) and also the comparative electrolyte containing 2% by weight of vinylene carbonate (VC).

As FIG. 5 shows, the electrolyte containing 2% by weight of 3-methyl-1,4,2-dioxoazol-5-one displayed good capacity retention at low temperatures, with the capacity after 100 cycles still being more than 80% of the capacity of cycle 6. In contrast, the comparative electrolyte displays only a very short cycling life of only 20 cycles to the EOL (end of life) criterion of 80% of the capacity of cycle 6 is reached.

This shows that 3-methyl-1,4,2-dioxoazol-5-one is, in contrast to vinylene carbonate, well suited to low-temperature applications and lithium ion batteries having 3-methyl-1,4,2-dioxoazol-5-one as additive can be operated with good cycling stability even at low temperatures.

The invention claimed is:

1. An electrolyte for an electrochemical energy store comprising an electrolyte salt and a solvent, characterized in that the electrolyte comprises at least one compound of the general formula (1) as indicated below:

(1)

where:
X is C, S or S=O;
R$^1$ is selected from the group consisting of CN, C$_1$-C$_{10}$-alkyl, C$_1$-C$_{10}$-alkoxy, C$_3$-C$_7$-cycloalkyl, C$_6$-C$_{10}$-aryl, —CO—O—R$^2$ and combinations thereof, wherein the alkyl, alkoxy, cycloalkyl and aryl groups are each unsubstituted or monosubstituted or polysubstituted by at least one substituent selected from the group consisting of F, C$_{1-4}$-alkyl, CN and mixtures thereof; and
R$^2$ is selected from the group consisting of C$_1$-C$_{10}$-alkyl, C$_3$-C$_7$-cycloalkyl, C$_6$-C$_{10}$-aryl and mixtures thereof.

2. The electrolyte as claimed in claim 1, characterized in that R$^1$ is selected from the group consisting of CN, C$_1$-C$_5$-alkyl, C$_1$-C$_5$-phenyl and mixtures thereof, wherein the C$_1$-C$_5$-alkyl and/or C$_1$-C$_5$-phenyl are unsubstituted or monosubstituted or polysubstituted by fluorine.

3. The electrolyte as claimed in claim 1, characterized in that X is carbon and R$^1$ is selected from the group consisting of CH$_3$, CF$_3$, CN, tert-butyl, phenyl and mixtures thereof.

4. The electrolyte as claimed in claim 1, characterized in that the electrolyte contains the compound of the general formula (1) in an amount in the range from ≥0.1% by weight to ≤10% by weight based on the total weight of the electrolyte.

5. The electrolyte as claimed in claim 1, characterized in that the electrolyte contains the compound of the general formula (1) in an amount in the range from ≥0.5% by weight to ≤7% by weight, based on the total weight of the electrolyte.

6. The electrolyte as claimed in claim 1, characterized in that the electrolyte contains the compound of the general formula (1) in an amount in the range from ≥3% by weight to ≤5% by weight, based on the total weight of the electrolyte.

7. The electrolyte as claimed in claim 1, characterized in that the solvent is selected from the group consisting of an unfluorinated organic solvent, a partially fluorinated organic solvent, an ionic liquid, a polymer matrix and mixtures thereof.

8. The electrolyte as claimed in claim 1, characterized in that the solvent is an organic solvent selected from the group consisting of ethylene carbonate, ethyl methyl carbonate, propylene carbonate, dimethyl carbonate, diethyl carbonate, acetonitrile, propionitrile, 3-methoxypropionitrile, glutaronitrile, adiponitrile, pimelonitrile, gamma-butyrolactone, gamma-valerolactone, dimethoxyethane, 1,3-dioxolane, methyl acetate, ethyl acetate, ethyl methanesulfonate, dimethyl methylphosphonate, linear sulfone, cyclic sulfone, symmetrical alkyl phosphates, unsymmetrical alkyl phosphates and mixtures thereof.

9. The electrolyte as claimed in claim 1, characterized in that the electrolyte salt is selected from the group consisting of $LiPF_6$, $LiBF_4$, $LiAsF_6$, $LiSbF_6$, $LiClO_4$, $LiPtCl_6$, $LiN(SO_2F)_2$, $LiN(SO_2CF_3)_2$, $LiN(SO_2C_2F_5)_2$, $LiC(SO_2CF_3)_3$, $LiB(C_2O_4)_2$, $LiBF_2(C_2O_4)$, $LiSO_3CF_3$ and mixtures thereof.

10. The electrolyte as claimed in claim 1 characterized in that the electrolyte salt is $LiPF_6$.

11. An electrochemical energy store comprising an electrolyte as claimed in claim 1.

12. An electrochemical energy store, wherein the electrochemical store is a supercapacitor comprising an electrolyte as claimed in claim 1.

13. An electrochemical energy store based on lithium, comprising an electrolyte as claimed in 1.

14. A method for forming a solid electrolyte interphase on an electrode of an electrochemical cell comprising an anode, a cathode and an electrolyte, wherein the cell is operated using an electrolyte as claimed in claim 1.

15. A method for preparing a stable solid electrolyte interphase for protecting graphite anodes against exfoliation comprising:

preparing a compound of the general formula (1) as indicated below:

where:

X is C, S or S=O;

$R^1$ is selected from the group consisting of CN, $C_1$-$C_{10}$-alkyl, $C_1$-$C_{10}$-alkoxy, $C_3$-$C_7$-cycloalkyl, $C_6$-$C_{10}$-aryl, and/or —CO—O—$R^2$ and mixtures thereof, wherein the alkyl, alkoxy, cycloalkyl and aryl groups are each unsubstituted or monosubstituted or polysubstituted by at least one substituent selected from the group consisting of F, $C_{1-4}$-alkyl, CN and mixtures thereof and $R^2$ is selected from the group consisting of $C_1$-$C_{10}$-alkyl, $C_3$-$C_7$-cycloalkyl, $C_6$-$C_{10}$-aryl and mixtures thereof, using the compound in an electrochemical energy store.

16. The method of claim 15, wherein the electrochemical energy store is a supercapacitor or an electrochemical energy store based on lithium ions.

17. The method of claim 15, wherein the electrochemical energy store is based on lithium ions.

* * * * *